(12) United States Patent
Ohashi et al.

(10) Patent No.: US 11,461,449 B2
(45) Date of Patent: Oct. 4, 2022

(54) BIOMETRIC AUTHENTICATION DEVICE

(71) Applicants: KABUSHIKI KAISHA TOKAI RIKA DENKI SEISAKUSHO, Aichi (JP); TOYOTA JIDOSHA KABUSHIKI KAISHA, Aichi-ken (JP)

(72) Inventors: Yosuke Ohashi, Aichi (JP); Rijin Owaki, Aichi (JP); Takahiko Ando, Aichi (JP); Yasuhisa Ohta, Aichi-ken (JP); Yuya Goto, Aichi-ken (JP); Naoyuki Takada, Aichi-ken (JP); Daisuke Ogawa, Aichi (JP)

(73) Assignees: KABUSHIKI KAISHA TOKAI RIKA DENKI SEISAKUSHO, Aichi (JP); TOYOTA JIDOSHA KABUSHIKI KAISHA, Aichi-Ken (JP)

( * ) Notice: Subject to any disclaimer, the term of this patent is extended or adjusted under 35 U.S.C. 154(b) by 0 days.

(21) Appl. No.: 17/271,937

(22) PCT Filed: Aug. 28, 2019

(86) PCT No.: PCT/JP2019/033783
§ 371 (c)(1),
(2) Date: Feb. 26, 2021

(87) PCT Pub. No.: WO2020/050115
PCT Pub. Date: Mar. 12, 2020

(65) Prior Publication Data
US 2021/0319086 A1    Oct. 14, 2021

(30) Foreign Application Priority Data
Sep. 4, 2018    (JP) .............................. JP2018-165270

(51) Int. Cl.
*G06F 21/32*    (2013.01)
*B60R 25/25*    (2013.01)
(Continued)

(52) U.S. Cl.
CPC ............ *G06F 21/32* (2013.01); *B60R 25/252* (2013.01); *G06V 40/1306* (2022.01); *G06V 40/1376* (2022.01); *G06V 40/63* (2022.01)

(58) Field of Classification Search
CPC .... G06F 21/32; G06V 40/63; G06V 40/1376; G06V 40/1306; B60R 25/252
See application file for complete search history.

(56) References Cited

U.S. PATENT DOCUMENTS

| | | | |
|---|---|---|---|
| 2003/0005336 A1* | 1/2003 | Poo | G06V 40/12 726/5 |
| 2014/0294259 A1 | 10/2014 | Lee | |
| 2018/0349939 A1* | 12/2018 | Setchell | G06V 20/52 |

FOREIGN PATENT DOCUMENTS

| | | |
|---|---|---|
| JP | 2002-298126 A | 10/2002 |
| JP | 2003-034235 A | 2/2003 |

(Continued)

OTHER PUBLICATIONS

Fernando Alonso-Fernandez et al: "A Comparative Study of Fingerprint Image-Quality Estimation Methods" IEEE Transactions on Information Forensics and Security, IEEE, USA, vol. 2, No. 4, Dec. 1, 2007 (Dec. 1, 2007), pp. 734-743, XP011196791, ISSN: 1556-6013, DOI: 10.1109/TIFS.2007.908228.

*Primary Examiner* — Nabil H Syed
(74) *Attorney, Agent, or Firm* — Roberts Calderon Safran & Cole P.C.

(57) ABSTRACT

A biometric authentication device includes a biometric information sensor to read biometric information of a user, a biometric information storage unit to pre-register biometric information of a registered person as registered biometric information for verification, a determination unit to determine whether or not a captured image captured by the biometric information sensor is suitable for biometric authentication, and to perform biometric authentication by (Continued)

comparing the captured image to the registered biometric information registered in the biometric information storage unit when the determination unit determines that the captured image is suitable for the biometric authentication, and a notification unit to issue a notification indicating that the captured image is unsuitable for the biometric authentication. When the determination unit determines that the captured image is unsuitable for the biometric authentication, the determination unit does not perform the biometric authentication by the authentication unit and causes the notification unit to issue the notification.

9 Claims, 5 Drawing Sheets

(51) Int. Cl.
*G06V 40/60* (2022.01)
*G06V 40/13* (2022.01)
*G06V 40/12* (2022.01)

(56) References Cited

FOREIGN PATENT DOCUMENTS

| JP | 2000-166900 A | 6/2006 |
|----|---------------|--------|
| JP | 2008-174095 A | 7/2008 |
| JP | 2017-052380 A | 3/2017 |

* cited by examiner

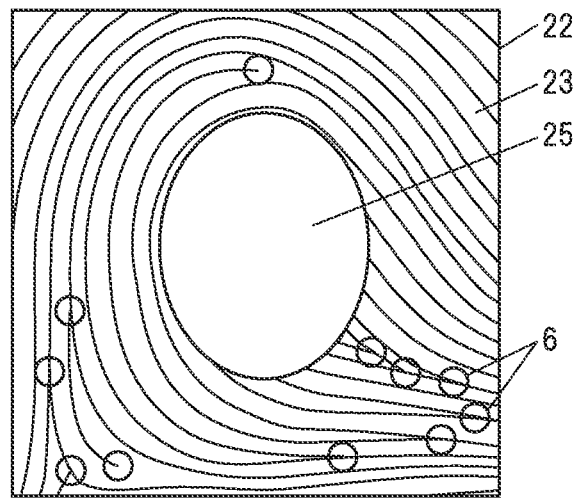
FIG. 4A
FIG. 4B
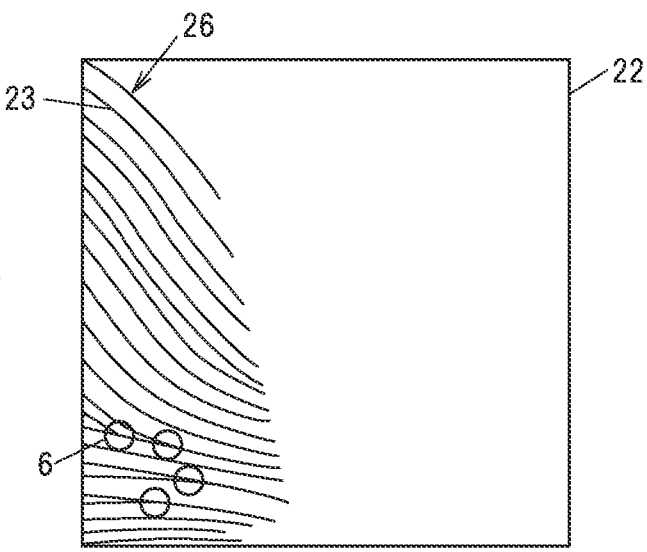
FIG. 4C

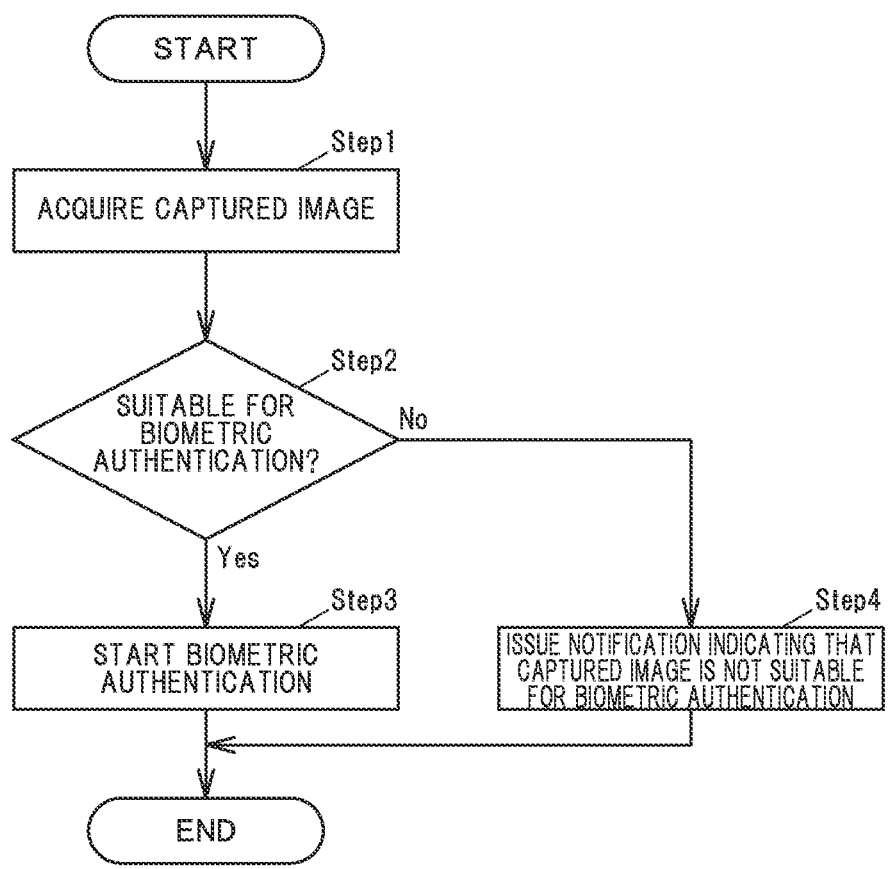

BIOMETRIC AUTHENTICATION DEVICE

CROSS-REFERENCE TO RELATED APPLICATIONS

The present application is a U.S. National Phase of PCT/JP2019/033783 filed on Aug. 28, 2019 claiming priority to Japanese Patent Application No. 2018-165270 filed on Sep. 4, 2018. The disclosure of the PCT Application is hereby incorporated by reference into the present Application.

The present invention relates to a biometric authentication device.

BACKGROUND ART

A start control device is known which is provided with a start switch giving an instruction to start or stop a drive source, a start-up means for starting the drive source, a fingerprint sensor for reading fingerprints, and a control means which, based on inputs from the fingerprint sensor and the start switch, implements a start-up process to control activation of the start-up means (see, e.g., Patent Literature 1).

When the start switch gives an instruction to start, the control means of the start control device performs fingerprint verification by comparing a fingerprint read by the fingerprint sensor with a pre-registered fingerprint before start-up by the start-up means, and once a match is found, the control means authenticates the user as a genuine user and allows the start-up means to start up.

CITATION LIST

Patent Literature

Patent Literature: JP 2008/174095 A

SUMMARY OF INVENTION

Technical Problem

In case of the start control device disclosed in Patent Literature 1, when, e.g., a read fingerprint is not suitable for biometric authentication because of a foreign matter such as a liquid sticking to a finger or the fingerprint sensor and biometric authentication is unsuccessful, the user does not know why it was unsuccessful and thus repeats unsuccessful attempts even if receiving a notification indicating that the biometric authentication result is unsuccessful biometric authentication. Therefore, there is a problem that it takes time until biometric authentication is successfully completed, hence, high operational burden.

It is an object of the invention to provide a biometric authentication device that can suppress operational burden.

Solution to Problem

According to an embodiment of the invention, a biometric authentication device comprises:
- a biometric information sensor to read biometric information of a user;
- a biometric information storage unit to pre-register biometric information of a registered person as registered biometric information for verification;
- a determination unit to determine whether or not a captured image captured by the biometric information sensor is suitable for biometric authentication, and to perform biometric authentication by comparing the captured image to the registered biometric information registered in the biometric information storage unit when the determination unit determines that the captured image is suitable for the biometric authentication; and
- a notification unit to issue a notification indicating that the captured image is unsuitable for the biometric authentication, wherein, when the determination unit determines that the captured image is unsuitable for the biometric authentication, the determination unit does not perform the biometric authentication and causes the notification unit to notify that the captured image is unsuitable for the biometric authentication.

According to an embodiment of the invention, it is possible to provide a biometric authentication device that suppresses operational burden.

BRIEF DESCRIPTION OF DRAWINGS

FIG. 4A is an explanatory diagram illustrating a captured image that a control unit of the start switch device in the embodiment determines unsuitable for biometric authentication.

FIG. 4B is an explanatory diagram illustrating a captured image that the control unit of the start switch device in a modification determines unsuitable for biometric authentication.

FIG. 4C is an explanatory diagram illustrating a captured image that the control unit of the start switch device in a modification determines unsuitable for biometric authentication.

FIG. 5 is a flowchart showing an operation of the start switch device in the embodiment.

DESCRIPTION OF EMBODIMENT

Summary of the Embodiment

A biometric authentication device in the embodiment has a determination unit that does not perform biometric authentication when determining that a captured image captured by a biometric information sensor provided to read biometric information of a user is unsuitable for biometric authentication, but instead outputs a notification signal to cause a notification unit to issue a notification indicating that the captured image is unsuitable for the biometric authentication.

When the captured image is not suitable for biometric authentication, this biometric authentication device notifies of it before performing biometric authentication.

Therefore, it is possible to find out and address a problem of the captured image at an early, stage, and it is thus possible to suppress operational burden, as compared to when the result of biometric authentication is notified.

Embodiment

General Configuration of a Start Switch Device 1

Figure 1A:
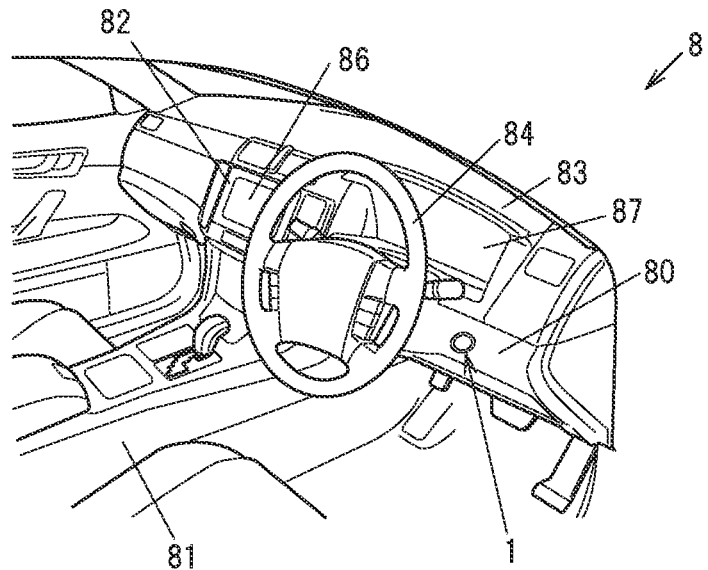
FIG. 1A is an explanatory diagram illustrating the inside of a vehicle in which a start switch device in an embodiment is arranged.
Figure 1B:
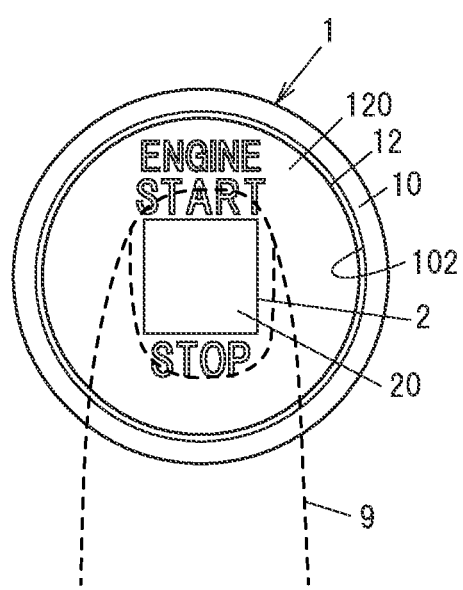
FIG. 1B is an explanatory diagram illustrating the start switch device in the embodiment.
Figure 2A:
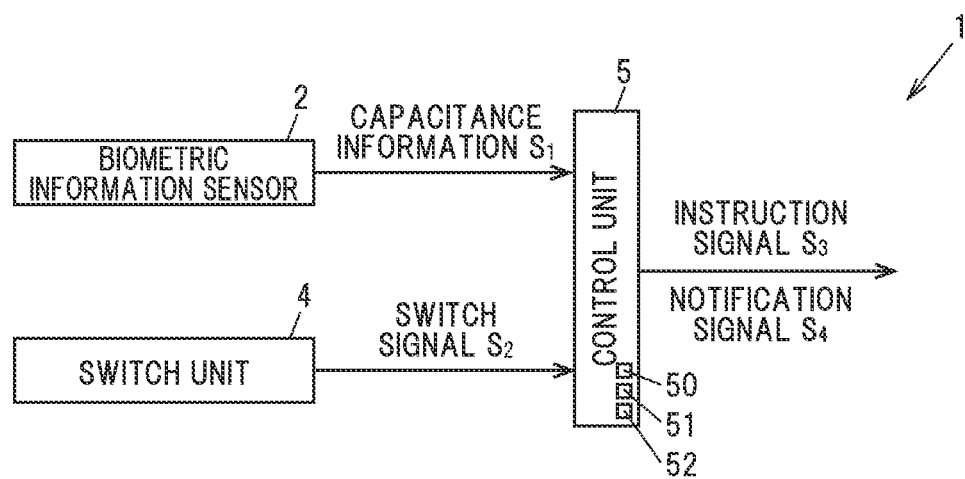
FIG. 2A is a block diagram illustrating the start switch device in the embodiment.
Figure 2B:
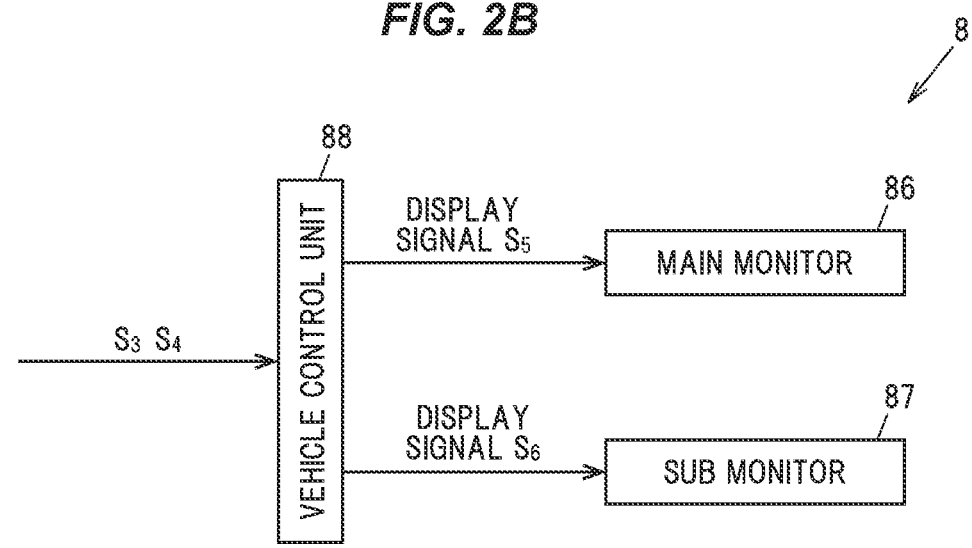
FIG. 2B is a block diagram illustrating the vehicle.
Figure 3A:
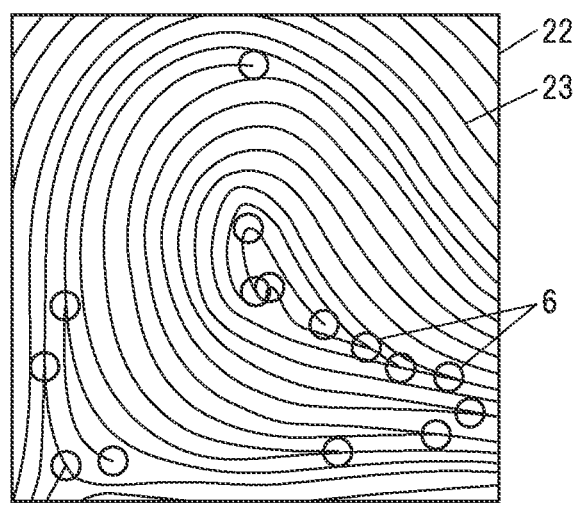
FIG. 3A is an explanatory diagram illustrating a captured image that is captured by a biometric information sensor of the start switch device in the embodiment.
Figure 3B:
FIG. 3B is an explanatory diagram illustrating a message that is issued by the start switch device in the embodiment and displayed on a main monitor.

FIG. 1A is an explanatory diagram illustrating the inside of a vehicle in which a start switch device in the embodiment is arranged, and FIG. 1B is an explanatory diagram the start switch device in the embodiment. FIG. 2A is a block diagram illustrating the start switch device in the embodiment and FIG. 2B is a block diagram illustrating the vehicle. FIG. 3A is an explanatory diagram illustrating a captured image that is captured by a biometric information sensor of the start switch device in the embodiment and FIG. 3B is an explanatory diagram illustrating a message that is issued by the start switch device in the embodiment and displayed on a main monitor.

In each drawing of the embodiment described below, a scale ratio may be different from an actual ratio. In addition, in FIGS. 2A and 2B, flows of main signals and information, etc., are indicated by arrows.

As shown in FIG. 1A, the start switch device 1 as the biometric authentication device is arranged on, e.g., a panel 80 located in front of a user sitting in a driver's seat and at the periphery of a steering wheel 84, a floor console 81 located between the driver's seat and the front passenger seat, or the steering wheel 84, etc. This start switch device 1 can instruct a vehicle control unit 89 of a vehicle 8 to start, or to prepare to start, a drive system of the vehicle 8 by a push operation (ON operation), and instruct to stop the drive system by a next push operation (OFF operation).

Start-up of the drive system of the vehicle 8 and the power state transition of the vehicle 8 are judged by, e.g., the vehicle control unit 89 based on an instruction signal $S_3$ output from the start switch device 1 and the operating conditions for a shifting device, etc. In this regard, the biometric information device is not limited to the start switch device 1 and can be mounted on a device that performs biometric authentication for login, unlock or payment.

The start switch device 1 has, e.g., a control unit 5 as a determination unit that does not perform biometric authentication when determining that a captured image 22 captured by a biometric information sensor 2 provided to read biometric information 23 of a user is unsuitable for biometric authentication, but instead outputs a notification signal $S_4$ to cause a notification unit to issue a notification indicating that the captured image 22 is unsuitable for the biometric authentication, as shown in FIGS. 1B and 2A.

The control unit 5 is configured to determine that the captured image 22 is unsuitable for the biometric authentication when the number of characteristic features 6 (described later) extracted from the captured image 22 is not more than a notification threshold value 52 as the first notification threshold value.

As shown in FIGS. 1B and 2A, the start switch device 1 is also provided with e biometric information sensor 2 and a switch unit 4, as an example.

As shown in FIG. 1B, this start switch device 1 is provided with, e.g., a cylindrical main body 10 and an operation button 12. The operation button 12 is inserted into an opening 102 of the main body 10.

Meanwhile, as an example, the vehicle 8 is provided with a main monitor 86, a sub monitor 87 and the vehicle control unit 89, as shown in FIG. 2B. The notification unit in the present embodiment is at least one of the main monitor 86 and the sub monitor 87, but it is not limited thereto. In addition, the notification unit is not limited to, e.g., the main monitor 86 or the sub monitor 87 and may be a speaker device that output sound. In addition, the notification may be issued by, e.g., a combination of at least two of the main monitor 86, the sub monitor 87 and a speaker device.

As an example, the main monitor 86 is arranged on a center console 82 as shown in FIG. 1A, but it is not limited thereto. The main monitor 86 is, e.g., a liquid crystal monitor and carries out display based on a display signal $S_5$ output from the vehicle control unit 89.

As an example, the sub monitor 87 is arranged on an instrument panel 83 in front of the driver's seat as shown in FIG. 1A, but it is not limited thereto. The sub monitor 87 is, e.g., a liquid crystal monitor and carries out display based on a display signal $S_6$ output from the vehicle control unit 89. The position for arranging the sub monitor 87 is not limited to, e.g., the instrument panel 83 and may be another position such as a head-up display, etc. In the following description, the notification unit is the main monitor 86.

The vehicle control unit 89 is, e.g., a microcomputer composed of a CPU (Central Processing Unit), and a RAM (Random Access Memory) and a ROM (Read Only Memory) as semiconductor memories, etc. The vehicle control unit 89 is electromagnetically connected to the start switch device 1 via, e.g., an in-vehicle LAN (Local Area Network) such as CAN (Controller Area Network) or LIN (Local Interconnect Network).

Configuration of the Biometric Information Sensor 2

The biometric information sensor 2 is configured to read, e.g., a fingerprint of an operating linger 9 as the biometric information 23, as shown in FIGS. 1B and 3A. However, the biometric information 23 is not limited to the fingerprint of the operating finger 9 and may be a vein of the operating finger 9, etc.

In case of reading, e.g., a fingerprint of the operating finger 9, the biometric information sensor 2 used here is a sensor of optical, capacitive, electric field strength measuring, pressure-sensitive, or thermal type, etc., which is configured to read a fingerprint.

Meanwhile, in case of reading, e.g., a vein of the operating finger 9, the biometric information sensor 2 used is a sensor configured to read a vein based on reflection of emitted infrared radiation.

Then, in case of reading, e.g., both a fingerprint and a vein, the biometric information sensor 2 used is a sensor configured to extract a fingerprint and a vein by processing an image captured under visible light.

The biometric information sensor 2 in the present embodiment is, e.g., a capacitive sensor that reads a fingerprint as the biometric information 23. This biometric information sensor 2 is configured to read the biometric information 23 from the operation finger 9 which is in contact with a reading surface 20 when an operator touches an operation surface 120 of the operation button 12.

Alternatively, the reading surface 20 may be arranged under the operation surface 120 without being exposed on the operation surface 120. In addition, the shape of the reading surface 20 is not limited to, e.g., a rectangle and may be a circle or an ellipse.

The biometric information sensor 2 is provided with, e.g., plural detection electrodes which are arranged in rows and columns in a grid pattern under the reading surface 20. As an example, several ten thousand to several hundred thousand detection electrodes are formed and arranged at intervals of several μm to several tens μm.

The biometric information sensor 2 is configured to scan all detection electrodes by, e.g., repeating a process of reading capacitances of the detection electrodes arranged in one row while changing columns and then subsequently reading capacitances of the detection electrodes arranged in a different row. The scanning cycle is about 100 ms, as an example.

The biometric information sensor 2 outputs, e.g., capacitance information $S_1$, which is generated based on plural capacitances read by scanning, to the control unit 5. The capacitance information $S_1$ is generated based on, e.g., capacitances in one cycle.

In particular, the biometric information sensor 2 generates the capacitance information $S_1$ by, e.g., classifying the capacitances into binary values in such a manner that capacitances of not less than a predetermined threshold value are assigned "1" and capacitances of less than the threshold value are assigned "0", and then associating the capacitances with the positions of the detection electrodes.

The captured image 22 shown in FIG. 3A is obtained based on the capacitance information $S_1$ and is produced in such a manner that the positions of the detection electrodes assigned "1" described above are shown in black and the positions of the detection electrodes assigned "0" are shown in white, as an example. The circles in the drawing are added to show some of the characteristic features 6 (described later).

The high-capacitance positions are positions of ridges of the fingerprint which are close to the detection electrodes, hence, capacitance is high. Meanwhile, the low-capacitance positions are positions of valleys of the fingerprint which are far from the detection electrodes, hence, capacitance is low. Therefore, as an example, the captured image 22 shown in FIG. 3A is obtained when the high-capacitance positions are shown in black and the low-capacitance positions are shown in white. The image shown in black in the captured image 22 is the read biometric information 23.

Configuration of the Switch Unit 4

As an example, the switch unit 4 is configured as a rubber dome switch which comes into contact with an end portion of the operation button 12 on the opposite side to the operation surface 120. The rubber dome switch is provided with, e.g., a rubber dome which generates an elastic force and has a movable contact, and a switch substrate on which the rubber dome is arranged and which has a fixed contact facing the movable contact.

When the operation button 12 is pushed into the main body 10 by a push operation, the movable contact is electrically conducted to the fixed contact due to deformation of the rubber dome and a switch signal $S_2$, which indicates that the switch is turned on, is output to the control unit 5. The start switch device 1 is configured that when, e.g., the push operation ends, the operation button 12 returns to the initial position by an elastic force of the rubber dome.

Configuration of the Control Unit 5

FIG. 4A is an explanatory diagram illustrating a captured image that the control unit of the start switch device in the embodiment determines unsuitable for biometric authentication, and FIGS. 4B and 4C are explanatory diagrams illustrating captured images that the control unit of the start switch device in modifications determines unsuitable for biometric authentication. FIG. 4B is an explanatory diagram in which the captured image 22 as shown in FIG. 4A is shown in binary.

The control unit 5 is, e.g., a microcomputer composed of a CPU performing calculation and processing, etc., of the acquired data according to a stored program, and a RAM and a ROM as semiconductor memories, etc. The ROM stores, e.g., a program for operation of the control unit 5. The RAM is used as, e.g., a storage area for storing registered biometric information 50, an authentication threshold value 51, the notification threshold value 52, and calculation results, etc. In addition, the control unit 5 has, inside thereof, a means for generating a clock signal, and operates based on the clock signal.

The control unit 5 performs, e.g., an extraction process on the capacitance information $S_1$ and extracts the characteristic features 6. The extraction process is, e.g., a process of extracting fingerprint ridges, etc.

The characteristic feature 6 is, e.g., a center point, a bifurcation point, an ending point or a delta, etc., as shown in FIG. 3A, but it is not limited thereto. The center point is a point at the center of the fingerprint. The bifurcation point is a point at which a fingerprint ridge bifurcates. The ending point is a point at which a ridge ends. The delta is a point at which ridges from three directions meet.

The registered biometric information 50 is, e.g., information associating a registered person's name with a template. The registered person's name is, e.g., to identify a registered person who has registered the registered biometric information 50, and it is acquired from the vehicle 8. The template is composed of, e.g., the characteristic features 6 of the biometric information 23 that is read by the biometric information sensor 2. In this regard, the registered biometric information 50 is created for each biometric information 23 of the fingerprint registered by the user.

The control unit 5 compares, e.g., the characteristic features 6 of the read registered biometric information 23 of the user to the template of the registered biometric information 50 and calculates a degree of similarity based on the positions of the characteristic features 6 and distances between the characteristic features 6, etc. Then, when the degree of similarity is not less than the authentication threshold value 51, the control unit 5 outputs the instruction signal $S_3$ upon determination that the user is the registered person, i.e., the biometric information is successfully authenticated.

The authentication threshold value 51 is defined that the degree of similarity of the subject of comparison such as the positions of the characteristic features 6 and the distances between the characteristic features 6, etc., is 80%, as an example. In other words, when, e.g., the number of the subjects of comparison used for biometric authentication is eighty and when match is found for not less than sixty-four subjects of comparison, the control unit 5 determines that the user is the registered person.

The biometric authentication is not limited to being performed by the authentication method using the degree of similarity of the characteristic features 6 and may be performed by an authentication method such as pattern matching.

The notification threshold value 52 is a threshold for determining whether or not the captured image 22 is suitable for biometric authentication. The captured image 22 which can be used for biometric authentication means that, e.g., the captured image 22 has many characteristic features 6 and is thus good enough to be compared to the registered biometric information 50. As such, the notification threshold value 52 is a threshold related to the number of the characteristic features 6.

When, e.g., the degree of similarity of the subjects of comparison based on the positions of the characteristic features 6 and the distances between the characteristic features 6, etc., is not less than the authentication threshold value 51, the control unit 5 determines that biometric authentication is successful, as described above. The calculation of the positions of the characteristic features 6 and the distances between the characteristic features 6, etc., places a heavier load on the CPU and takes longer time than when counting the number of the characteristic features 6.

When notified that, e.g., a result of biometric authentication based on the calculation of the positions of the characteristic features 6 and the distances between the characteristic features 6, etc. . . . by the control unit 5 is unsuccessful, the user needs to touch the biometric information sensor 2 with his/her finger again. If, e.g., the user performs many biometric authentication attempts without knowing why biometric authentication is unsuccessful, it takes long time until biometric authentication is successfully completed, and operational burden also increases.

The captured image 22, which is read in a state that, e.g., a foreign matter such as liquid is sticking to the reading surface 20 of the biometric information sensor 2 or a foreign matter is sticking to the finger of the user, is highly likely an image that has a blank area 25 and is unsuitable for biometric authentication. Then, if the number of the characteristic features 6 in the captured image 22 is, e.g., obviously small without calculating the positions and the distances, biometric authentication is highly likely to be unsuccessful.

Accordingly, the control unit 5 is configured to count the number of the characteristic features 6 and determines, before performing biometric authentication, whether or not the captured image 22 is suitable for biometric authentication based on the notification threshold value 52.

When, the number of the characteristic features 6 is not more than the notification threshold value 52, the control unit 5 outputs the notification signal $S_4$ to the vehicle control unit 89. Based on the input notification signal $S_4$, the vehicle control unit 89 causes, e.g., a message image 861, which indicates that the captured image 22 is unsuitable for the biometric authentication, to be displayed on a display screen 860 of the main monitor 86, as shown in FIG. 3B.

This message image 861 is "The image is not usable for biometric authentication, wipe your finger, wipe the sensor.", as an example.

Here, the control unit 5 as a modification is configured to determine that the captured image 22 is unsuitable for biometric authentication when a difference between the number of first values and the number of second values in the captured image 22, which is shown in binary using the first value and the second value, is not less than the notification threshold value 52 (the second notification threshold value).

The first value and the second value are, e.g., "0" and "1" described earlier. Meanwhile, the notification threshold value 52 in this modification is, e.g., a threshold related to the difference between "0"s and "1"s. For example, FIG. 4B shows a part of detection electrodes each of which is provided with a binary value of "0" or "1".

When, e.g., a foreign matter is sticking to the finger or the reading surface 20, the blank area 25 is formed in the captured image 22, as shown in FIG. 4A. If, e.g., the foreign matter is not conductive, the blank area 25 is filled with the values "0", resulting in that there are more "0"s than "1"s.

Meanwhile, when, e.g., a conductive foreign matter is sticking, the blank area 25 is filled with "1"s.

When, e.g., the difference between "0"s and "1"s is not less than the notification threshold value 52 as shown in FIG. 4B, the control unit 5 determines that the captured image 22 is unsuitable for biometric authentication. In this regard, taking into consideration also the deposition of the conductive foreign matter, the difference between "0"s and "1"s is an absolute value.

Here, the control unit 5 may be configured to determine that captured image 22 is unsuitable for biometric authentication when, e.g.,. "0"s and "1"s are not scattered, i.e., when it is not clear. In this case, it could be the deposition of foreign matters but could be malfunction of the biometric information sensor 2. Therefore, the control unit 5 may be configured to output the notification signal $S_4$ for notifying that the information sensor 2 is malfunctioning when the similar determination is made plural times.

Meanwhile, the control unit 5 as another modification is configured to determine that the captured image 22 is unsuitable for the biometric authentication when an area of an image of the read biometric information 23 of the user is not more than the notification threshold value 52 (the third notification threshold value). This area is calculated as, e.g., the number of detection electrodes assigned "0" or "1".

The notification threshold value 52 in this modification is a threshold related to the area of the biometric information 23. FIG. 4C shows an image 26 of the biometric information 23 that has a small area, as an example. The area of the image 26 of the biometric information 23 is small also when, there is the blank area 25 as shown in FIG. 4A. When the area of the image of the biometric information 23 is small in such a manner, the number of the characteristic features 6 to be obtained is small.

The control unit 5 is configured to determine that the captured image 22 is unsuitable for biometric authentication when the area of the biometric information 23 is not more than the notification threshold value 52.

Further alternatively, the control unit 5 may be configured to determine whether or not the captured image 22 is suitable for biometric authentication based on a combination of at least two of the condition related to the number of the characteristic features 6, the condition related to the difference between the binary values, and the condition related to the area which are described above.

Next, an example of an operation of the start switch device 1 in the present embodiment will be described along with the flowchart of FIG. 5. An operation to determine whether or not the captured image 22 is suitable for biometric authentication will be described below.

Operation

The control unit 5 acquires the captured image 22 that is captured when the user touched the operation button 12 of the start switch device 1 (Step 1).

Next, the control unit 5 determines whether or not the acquired captured image 22 is suitable fix biometric authentication. The control unit 5 extracts the characteristic features 6 from the captured image 22 and determines that the captured image 22 is suitable for biometric authentication when the number of the extracted characteristic features 6 is more than the notification threshold value 52 (Step 2: Yes).

Next, the control unit 5 starts biometric authentication based on its determination that the captured image 22 is suitable for biometric authentication (Step 3), and then ends the operation to determines whether or not the captured image 22 is suitable for biometric authentication.

Meanwhile, when the number of the characteristic features 6 in the captured image 22 is not more than the notification threshold value 52 in Step 2, the control unit 5 determines that the captured image 22 is unsuitable for biometric authentication (Step 2: No) and outputs the notification signal $S_4$ to notify that the captured image 22 is unsuitable for biometric authentication (Step 4).

Effects of the Embodiment

The start switch device 1 in the present embodiment can suppress operational burden. In particular, when the captured image 22 is not suitable for biometric authentication, the start switch device 1 notifies of it before performing biometric authentication, Therefore, the user can find out and address a problem of the captured image 22 at an early stage, time to successful biometric authentication is reduced and it is thus possible to suppress operational burden, as compared to when the result of biometric authentication is notified.

Before performing biometric authentication, the start switch device 1 can make the main monitor 86, etc., to display the message image 861 indicating that the captured image 22 is unsuitable for the biometric authentication, thereby notifying the user of the deposition of a foreign matter, etc. Therefore, as compared to when not issuing a notification, the user can easily take measures such as wiping the reading surface 20 of the biometric information sensor 2 or wiping the finger, and thus can be successfully biometrically authenticated at an early stage.

Although some embodiment and modifications of the invention have been described, these embodiment and modifications are merely examples and the invention according to claims is not to be limited thereto. These new embodiment and modifications may be implemented in various other forms, and various omissions, substitutions and changes, etc., can be made without departing from the gist of the invention. In addition, all combinations of the features described in these embodiment and modifications are not necessary to solve the problem of the invention. Further, these embodiment and modifications are included within the scope and gist of the invention and also within the invention described in the claims and the range of equivalency.

REFERENCE SIGNS LIST

1 START SWITCH DEVICE
2 BIOMETRIC INFORMATION SENSOR
5 CONTROL UNIT
6 CHARACTERISTIC FEATURE
20 READING SURFACE
22 CAPTURED IMAGE
23 BIOMETRIC INFORMATION
50 REGISTERED BIOMETRIC INFORMATION
51 AUTHENTICATION THRESHOLD VALUE.
52 NOTIFICATION THRESHOLD VALUE
86 MAIN MONITOR
87 SUB MONITOR
860 DISPLAY SCREEN
861 MESSAGE IMAGE

The invention claimed is:
1. A biometric authentication device, comprising:
a biometric information sensor to read biometric information of a user;
a biometric information storage unit to pre-register biometric information of a registered person as registered biometric information for verification;
a determination unit to determine whether or not a captured image captured by the biometric information sensor is suitable for biometric authentication, and to perform biometric authentication by comparing the captured image to the registered biometric information registered in the biometric information storage unit when the determination unit determines that the captured image is suitable for the biometric authentication; and
a notification unit to issue a notification indicating that the captured image is unsuitable for the biometric authentication,
wherein, when the determination unit determines that the captured image is unsuitable for the biometric authentication, the determination unit does not perform the biometric authentication and causes the notification unit to notify that the captured image is unsuitable for the biometric authentication,
wherein the biometric information sensor reads a plurality of capacitances of a plurality of detection electrodes provided under a reading surface, classifies the plurality of capacitances into binary values in such a manner that capacitances of not less than a first predetermined threshold value are assigned a first value and capacitances of less than the first threshold value are assigned a second value, and generates capacitance information by associating the capacitances with the positions of the detection electrodes, thereby producing the captured image,
wherein, when a difference between the number of the first values and the number of the second values is not less than a second notification threshold value, the determination unit determines that the captured image is unsuitable for the biometric authentication.

2. The biometric authentication device according to claim 1, wherein the determination unit extracts characteristic features of the biometric information by performing an extraction process on the captured image, compares the characteristic features extracted from the captured image to the registered biometric information and, when a degree of similarity based on the characteristic features is not less than a similarity threshold value, successfully completes biometric authentication upon determination that the user is the registered person.

3. The biometric authentication device according to claim 2, wherein, when the number of the characteristic features is not more than a first notification threshold value, the determination unit determines that the captured image is unsuitable for the biometric authentication.

4. The biometric authentication device according to claim 2, wherein the biometric information sensor reads a fingerprint as the biometric information, and the determination unit extracts a center point, bifurcation points, ending points and deltas of the fingerprints as the characteristic features.

5. The biometric authentication device according to claim 1, wherein, when dispersion of distributions of the first value and the second value is not more than a predetermined degree of dispersion, the determination unit determines that the captured image is unsuitable for the biometric authentication.

6. The biometric authentication device according to claim 1, wherein the determination unit calculates an area of an image of the biometric information of the user and determines that the captured image is unsuitable for the biometric authentication when the calculated area of the image of the biometric information of the user is not more than a third notification threshold value.

7. The biometric authentication device according to claim 6, wherein the determination unit calculates the area of the image of the biometric information of the user as the number of the detection electrodes of the biometric sensor that are assigned the first value or the second value.

8. The biometric authentication device according to claim 1, wherein the notification unit issues a notification using sound, display, or a combination of sound and display.

9. A biometric authentication device, comprising:
a biometric information sensor to read biometric information of a user;
a biometric information storage unit to pre-register biometric information of a registered person as registered biometric information for verification;
a determination unit to determine whether or not a captured image captured by the biometric information sensor is suitable for biometric authentication, and to perform biometric authentication by comparing the captured image to the registered biometric information registered in the biometric information storage unit when the determination unit determines that the captured image is suitable for the biometric authentication; and
a notification unit to issue a notification indicating that the captured image is unsuitable for the biometric authentication,
wherein, when the determination unit determines that the captured image is unsuitable for the biometric authentication, the determination unit does not perform the biometric authentication and causes the notification unit to notify that the captured image is unsuitable for the biometric authentication,
wherein the biometric information sensor reads a plurality of capacitances of a plurality of detection electrodes provided under a reading surface, classifies the plurality of capacitances into binary values in such a manner that capacitances of not less than a first predetermined threshold value are assigned a first value and capacitances of less than the first threshold value are assigned a second value, and generates capacitance information by associating the capacitances with the positions of the detection electrodes, thereby producing the captured image,
wherein the determination unit calculates an area of an image of the biometric information of the user and determines that the captured image is unsuitable for the biometric authentication when the calculated area of the image of the biometric information of the user is not more than a third notification threshold value,
wherein the determination unit calculates the area of the image of the biometric information of the user as the number of the detection electrodes of the biometric sensor that are assigned the first value or the second value.

* * * * *